(12) United States Patent
Furnish

(10) Patent No.: US 7,292,715 B2
(45) Date of Patent: Nov. 6, 2007

(54) DISPLAY OF DIAGNOSTIC DATA

(75) Inventor: Simon Furnish, New York, NY (US)

(73) Assignee: InfraReDx, Inc., Burlington, MA (US)

( * ) Notice: Subject to any disclaimer, the term of this patent is extended or adjusted under 35 U.S.C. 154(b) by 853 days.

(21) Appl. No.: 10/457,812

(22) Filed: Jun. 9, 2003

(65) Prior Publication Data

US 2004/0247164 A1 Dec. 9, 2004

(51) Int. Cl.
*G06K 9/00* (2006.01)
(52) U.S. Cl. ........................... 382/128; 345/629
(58) Field of Classification Search ............... 382/128, 382/284, 294; 345/629, 630, 632, 634; 128/922
See application file for complete search history.

(56) References Cited

U.S. PATENT DOCUMENTS

| | | | | |
|---|---|---|---|---|
| 6,129,667 A | | 10/2000 | Dumoulin et al. | ............ 600/424 |
| 6,346,940 B1 | * | 2/2002 | Fukunaga | ................... 345/427 |
| 6,485,482 B1 | | 11/2002 | Belef | ........................ 604/528 |
| 6,891,963 B1 | * | 5/2005 | Goto et al. | ................... 382/131 |
| 7,162,066 B2 | * | 1/2007 | Oosawa | ...................... 382/132 |
| 2002/0173783 A1 | | 11/2002 | Ohno et al. | ..................... 606/10 |
| 2002/0183723 A1 | | 12/2002 | Belef et al. | ...................... 606/1 |
| 2003/0018235 A1 | | 1/2003 | Chen et al. | .................. 600/109 |

FOREIGN PATENT DOCUMENTS

| | | |
|---|---|---|
| EP | 1 086649 A1 | 3/2001 |
| WO | WO 02/41767 A1 | 5/2002 |
| WO | WO 02/082375 A2 | 10/2002 |

OTHER PUBLICATIONS http://www.accumedsystemsinc.com/products.html (Apr. 10, 2003).
International Search Report, PCT/US2004/017018, mailed on Oct. 1, 2004, 12 pages.

* cited by examiner

*Primary Examiner*—Andrew W. Johns
(74) *Attorney, Agent, or Firm*—Fish & Richardson P.C.

(57) ABSTRACT

A system for displaying diagnostic data includes a display on which is displayed an image having an anatomic map and a diagnostic map. The diagnostic map, which is disposed at a location indicative of the spatial distribution of the diagnostic data, shows a spatial distribution of that data.

12 Claims, 7 Drawing Sheets

DISPLAY OF DIAGNOSTIC DATA

FIELD OF INVENTION

This invention relates to catheters, and in particular, to catheters that scan the wall of a lumen.

BACKGROUND

In assessing a patient's vascular health, it is often useful to collect diagnostic data from an interior wall of a lumen. In known intravascular diagnostic systems, a scanning catheter having a detector at its distal end is coupled at its proximal end to a motor that rotates and translates the catheter at known rates. This enables the detector to circumferentially and axially scan the interior wall, collecting diagnostic data as it does so.

Because the rates at which the catheter rotates and translates are both known, a processor receiving the diagnostic data from the detector is able to infer the location from which the diagnostic data is retrieved and to associate that location with the diagnostic data. The processor then displays a diagnostic map showing the diagnostic data as a function of location on the arterial wall.

In such a system, the scanning of the wall is driven by a motor that moves the catheter at a known rate. Hence, the position of the catheter is inferred from the known rate and the elapsed time.

SUMMARY

In one aspect, the invention includes a method for generating a diagnostic map indicative of diagnostic data collected by a catheter from a target region. In such a method the catheter is moved manually to scan the target region, thereby collecting diagnostic data. As the catheter is moved, position data indicative of movement of the catheter is acquired. The position data and the diagnostic data are then associated to form a map.

One practice of the foregoing method includes manually moving the catheter in two dimensions by, for example, translating and rotating the catheter. In this case, the acquisition of position data includes the acquisition of rotation and translation data.

The invention also includes a system for displaying diagnostic data. Such a system has a display on which is displayed an image that includes an anatomic map and a diagnostic map. The diagnostic map is positioned relative to the anatomic map to show a spatial distribution of the diagnostic data.

In one embodiment, the image includes a detail portion spatially removed from the anatomic map. The detail portion shows a detailed view of a diagnostic map disposed on a portion of the anatomic map. The system can also include a mechanism for selecting a portion of the anatomic map on which is disposed the diagnostic map to be displayed in the detail portion.

In another embodiment. the system is configured to display the diagnostic map concurrently with acquisition of the diagnostic data. One way to configure the system in this way is to configure a cursor to move relative to the diagnostic map such that the position of the cursor relative the diagnostic map indicates a spatial location at which diagnostic data is currently being acquired.

The invention also includes a computer-readable medium on which is encoded software for causing a computer to display a spatial distribution of diagnostic data. The software includes instructions for causing a computer to display an anatomic map, and to overlay, at a location indicative of a spatial distribution of the diagnostic data on the anatomic map, a diagnostic map.

In one embodiment, the software includes instructions for causing the computer to display a detail portion spatially removed from the anatomic map. The detail portion shows a detailed view of a diagnostic map disposed on a portion of the anatomic map.

In another embodiment, the software includes instructions for causing the computer to select the portion of the anatomic map on which is disposed the diagnostic map to be displayed in the detail portion.

In yet another embodiment, the software includes instructions for causing the computer to display the diagnostic map concurrently with acquisition of the diagnostic data.

Other embodiments include those in which the software includes instructions for causing a cursor to move relative to the diagnostic map. In these embodiments, the position of the cursor relative the diagnostic map indicates a spatial location at which diagnostic data is currently being acquired.

DETAILED DESCRIPTION

Figure 1:
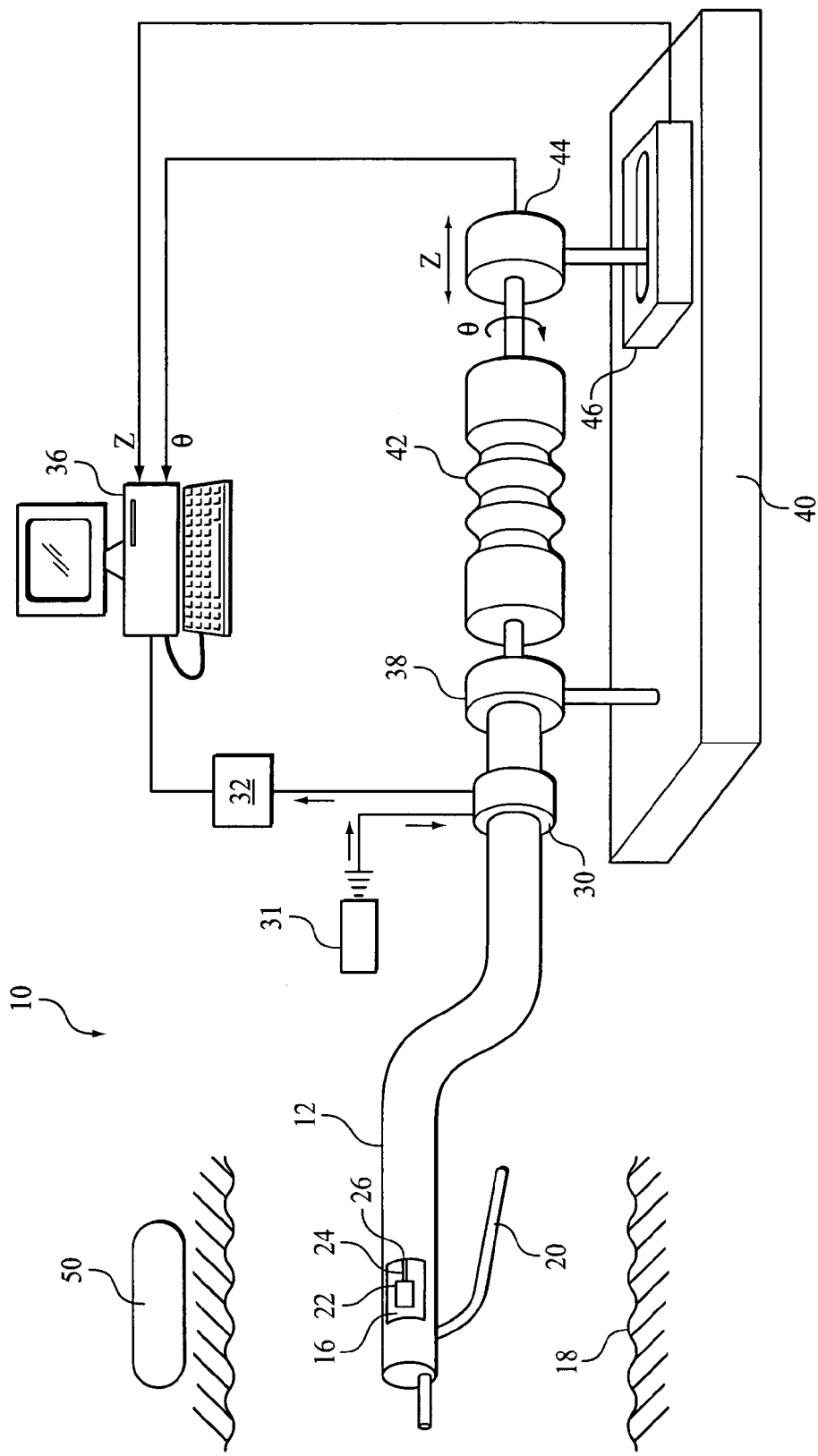
FIG. 1 is a schematic of a diagnostic system.

Referring to FIG. 1, a diagnostic system 10 according to the invention includes a scanning catheter 12 having, at a distal portion thereof, a transparent window 16 facing radially outward. The catheter 12 is configured to be rotated so that the view provided by the transparent window 16 sweeps around a circumferential path, thereby enabling a circumferential scan of a lumen's interior wall 18. A guide wire 20 passing through a distal portion of the catheter 12 guides back-and-forth, or longitudinal motion of the catheter 12, thereby enabling a longitudinal scan of the lumen's interior wall 18.

Within the catheter 12, and in optical communication with the window 16, is an optical bench assembly 22. A delivery fiber 24 and a collection fiber 26 optically coupled the bench assembly 22 to a coupling element 30 at a proximal end of the catheter 12. The coupling element 30 provides optical coupling between the delivery fiber 24 and a light source 31 and between the collection fiber 26 and an optical transducer 32. The optical transducer 32 transforms light from the delivery fiber 24 into data suitable for delivery to a processor 36. Exemplary optical bench assemblies 22 and coupling elements 30 are described in one or more of U.S. patent application Ser. Nos. 10/037,306 filed Dec. 31, 2002, and 10/164,721, filed Jun. 7, 2002, the contents of which are herein incorporated by reference.

A proximal portion of the catheter 12 passes through a catheter hub 38 mounted on a front end of a platform 40. Behind the hub 38, a handle 42 engages the catheter 12. Rotating the handle 42 rotates the catheter, and hence the transparent window 16. Translating the handle 42 translates the catheter 12, and hence the transparent window 16. The handle 42 thus provides manual control of both circumferential and axial scanning of the lumen's interior wall 18.

A rotation encoder 44 is mechanically coupled to the proximal end and in data communication with the processor 36. The rotation encoder 44 detects the extent and direction of rotation and provides a rotation signal, which contains this rotation information, to the processor 36.

The rotation encoder 44 is mechanically coupled to a translation encoder 46 mounted to a proximal end of the platform 40. Like the rotation encoder 44, the translation encoder 46 is in data communication with the processor 36. Axial translation of the handle 42 translates the rotation encoder 44 relative to the translation encoder 46. This enables the translation encoder 46 to detect the extent and direction of translation and to provide a translation signal containing this translation information to the processor 36.

Rotation encoders 44 and translation encoders 46 are examples of position encoders. Position encoders, which provide a signal indicative of position, are well known. For example, a computer mouse has a position encoder that detects relative motion in two-dimensions. Mechanical position encoders typically include a gear or wheel that turns in response to rotation of the handle 42 and another gear or wheel that turns in response to translation of the handle 42. These gears or wheels can operate potentiometers whose resistance can vary as a function of the movement of the gears or wheels.

Alternatively, the position encoder 44, 46 can be an optical device in which a beam illuminates a reflecting region having a spatially varying reflection coefficient. In the case of a translation encoder 46, the reflecting region is a plane. For a rotation encoder 44, a cylindrical reflecting region is mounted around a rotating shaft. In either case, a detector within the encoder 44, 46 detects fluctuations in a reflected beam and infers relative motion from those fluctuations.

Figure 2:
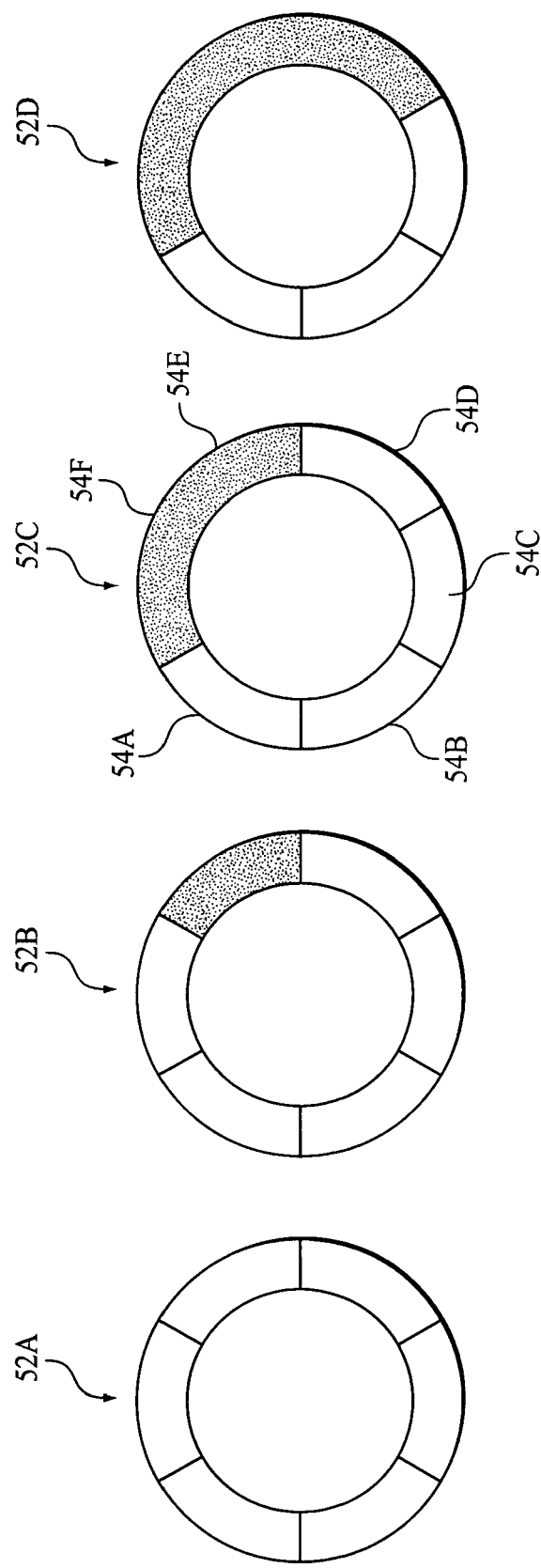
FIG. 2 is a map of diagnostic data collected by the diagnostic system of FIG. 1.

FIG. 2 shows exemplary diagnostic data collected in the vicinity of a lesion 50 within the interior wall 18. Each annulus 52A-D in FIG. 2 shows data collected at a particular longitudinal position of the catheter 12. The six sections 54A-F of an annulus 52C show data collected at six circumferential angles at the longitudinal position associated with that annulus 52C. The darkened sections 54E-F in each annulus correspond to circumferential angles at which the lesion 50 is located.

Figure 3:
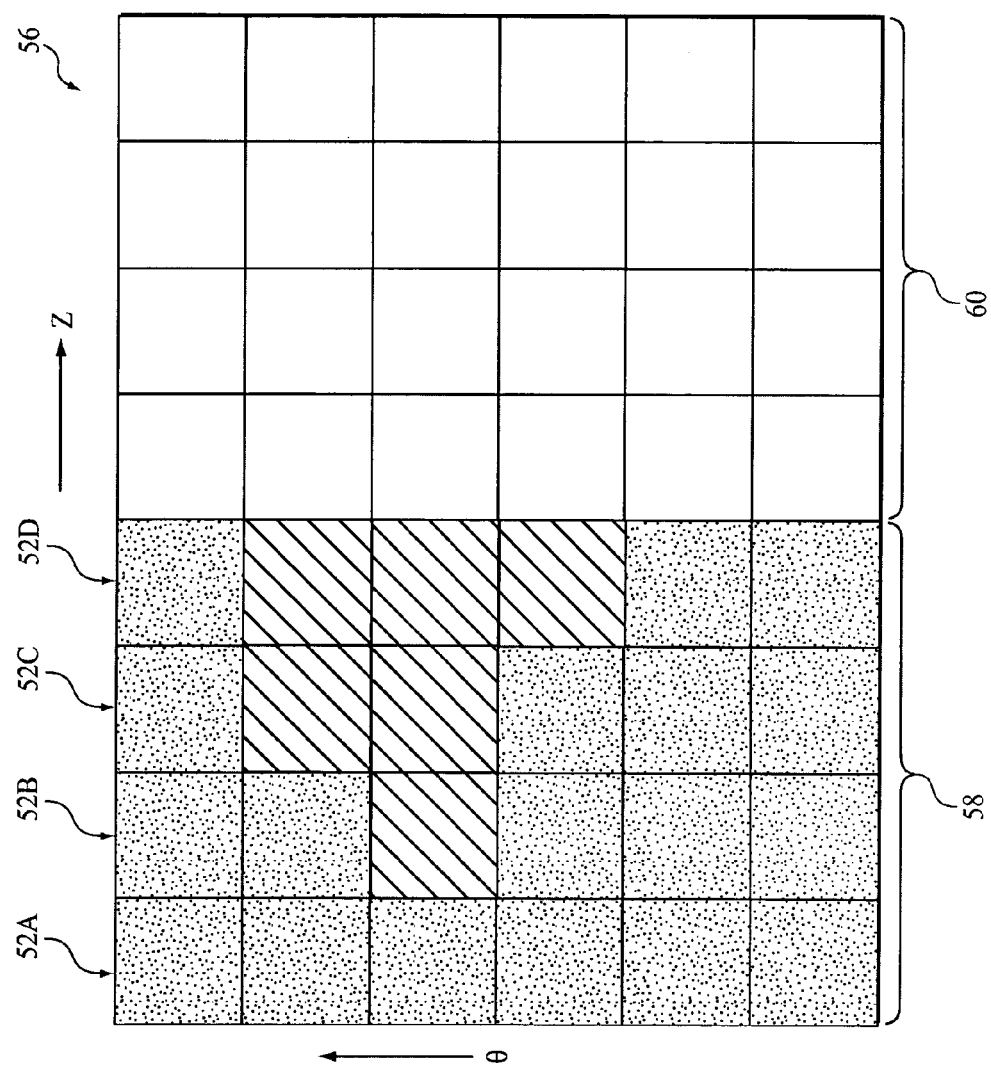
FIG. 3 is a schematic of second embodiment of a diagnostic system.

The processor 36 associates the diagnostic data shown in FIG. 2 with position data provided by the position encoders 44, 46. This results in a two dimensional diagnostic map 56, as shown in FIG. 3. This results in a two-dimensional diagnostic map 56, the vertical axis corresponds to the circumferential angle of the portion of the wall 18 from which the diagnostic data was collected. The horizontal axis corresponds to the longitudinal position of the that portion of the wall 18. The first four columns 58 on the left correspond to those portions of the wall 18 from which diagnostic data has already been acquired. The remaining four columns 60 correspond to those portions of the wall 18 from which diagnostic data has yet to be acquired.

Figure 4:
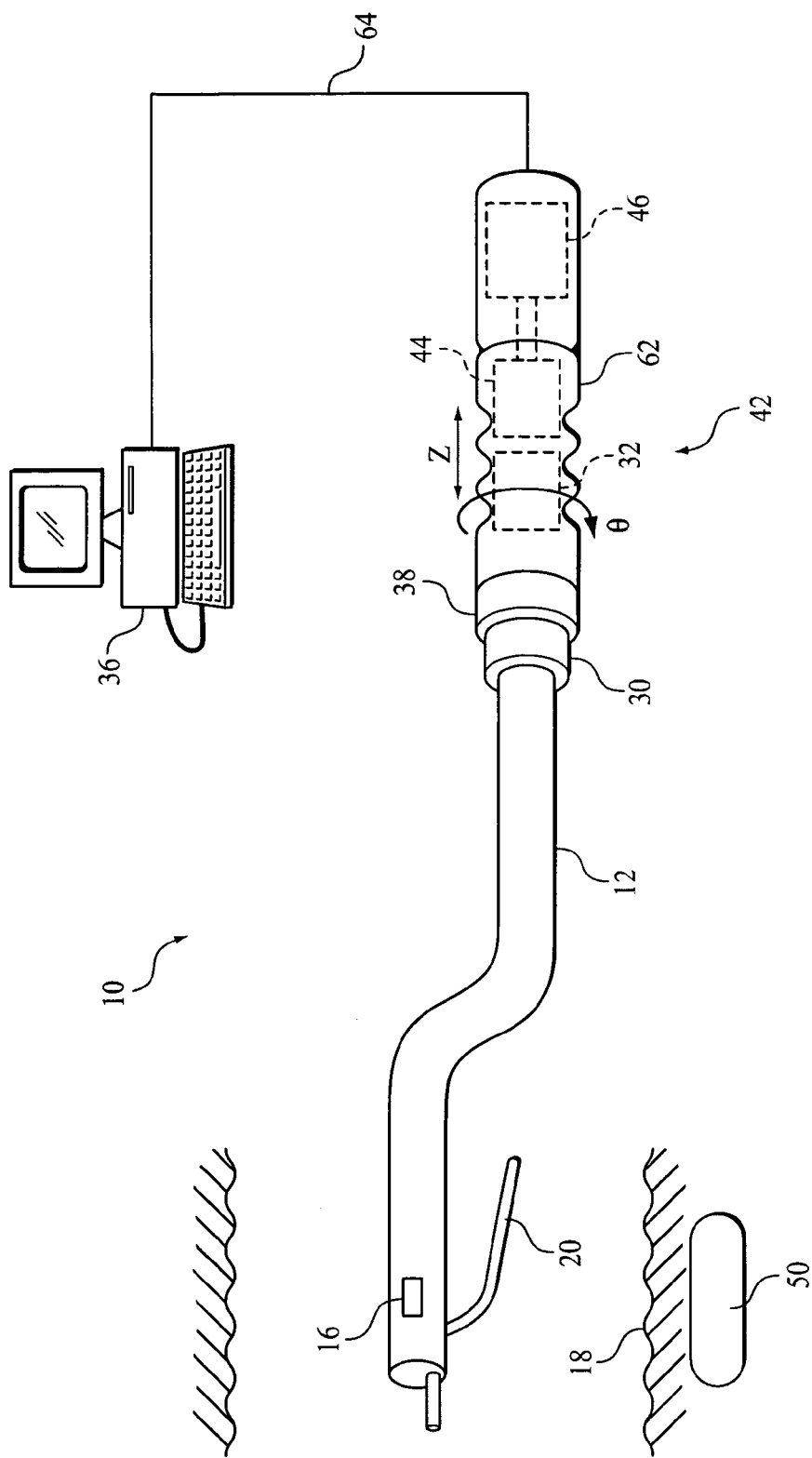
FIG. 4 is a schematic of a third embodiment of a diagnostic system.
Figure 5:
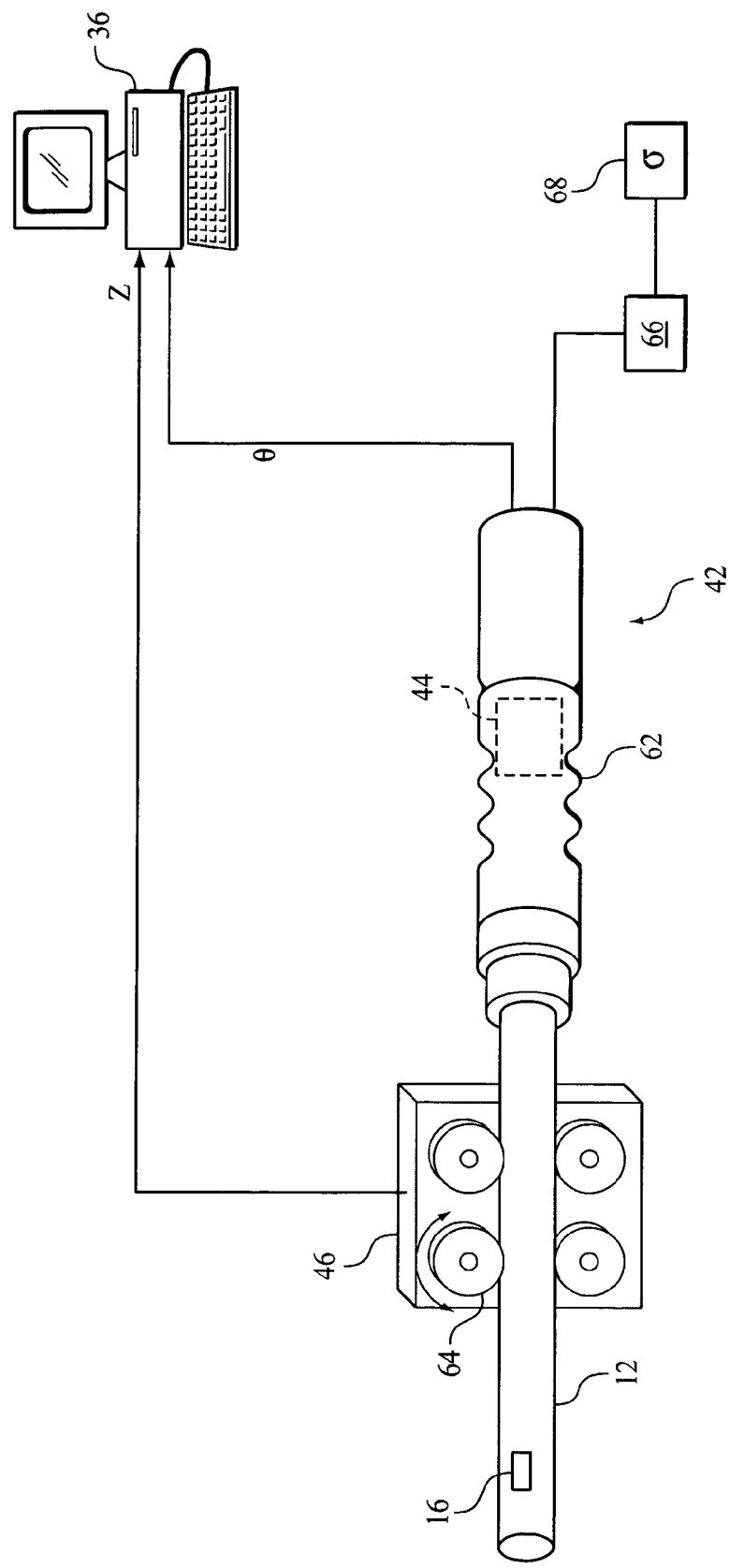
FIG. 5 is a representation of diagnostic data overlaid on an anatomic map of a patient's coronary arteries.

In a second embodiment, shown in FIG. 4, the handle 42 includes an actuator 62 that can be rotated and translated to cause rotation and translation of the catheter 12. A proximal end of the actuator 62 is coupled to a rotation encoder 44 integrated into the handle. The rotation encoder 44 is coupled to a translation encoder 46, also integrated into the handle 42. A cable 64 extending between the handle 42 and the processor 36 provides data communication for rotation and translation data and for diagnostic data received from the arterial wall 18. The processor 36 associates diagnostic data and both rotation and translation data in the manner already discussed in connection with FIGS. 2 and 3.

In a third embodiment, shown in FIG. 4, the translation encoder 46 includes a wheel 64 coupled to the catheter 12 so that translation of the catheter 12 causes rotation of the wheel 64 by an angle that depends on the extent of the translation. The processor 36 converts the angular rotation of the wheel 64 into translation data, which is then associated with diagnostic data as discussed above in connection with FIGS. 2 and 3.

The embodiments described thus far enable a surgeon to manually control both translation and rotation of the catheter 12. In some cases, it is more convenient to automatically rotate the catheter 12 while manually translating the catheter 12 (or vice versa). To accomplish this, an optional motor drive 66 coupled to the catheter 12 either rotates or translates the catheter 12. A switch 68 coupled to the motor drive 66 enables a surgeon to engage or disengage the motor drive 66 and to drive the catheter 12 either at a pre-selected rate or at a rate controllable by the surgeon during a diagnostic procedure.

To more clearly communicate the significance of diagnostic data, the diagnostic map 56 described in connection with FIGS. 2 and 3 is overlaid on an anatomic map 70 of the patient at a location consistent with the location from which the diagnostic data was collected.

Figure 6:
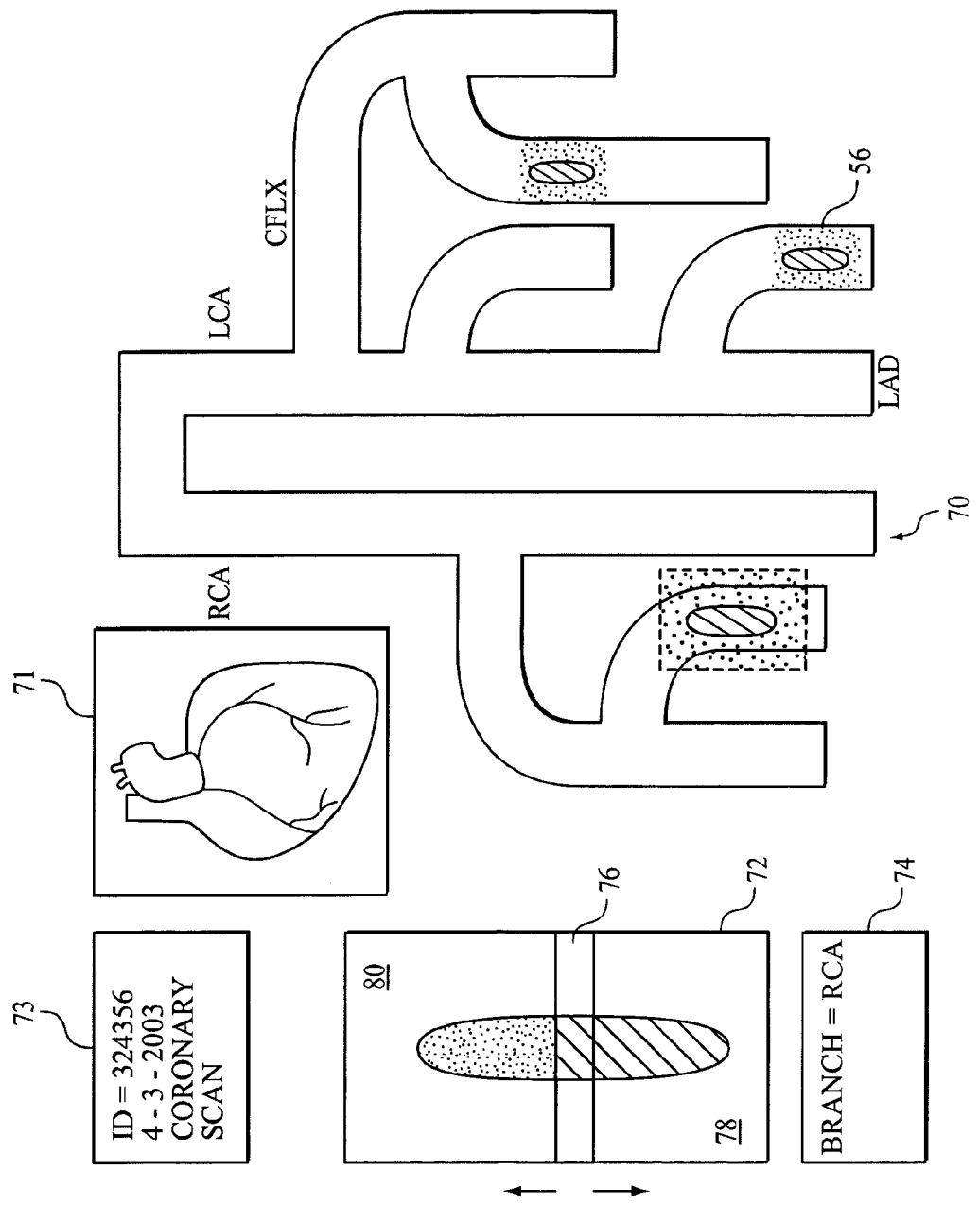
FIG. 6 is a display that includes an anatomic map of coronary arteries.

For example, FIG. 6 shows a display that includes an anatomic map 70 of a patient's coronary arteries. Although not to scale, the map shows the relative positions of the left and right coronary arteries ("LCA" and "RCA"), the circumflex artery ("CFLX"), the left anterior descending artery ("LAD") and other smaller arteries that deliver blood to various portions of the heart. Also shown on the display is an anatomically correct rendering 71 of the positions and extents of the coronary arteries on a typical heart. A patient-information window 73 shows information for identifying the patient and the type of procedure.

Diagnostic maps 56 of the type discussed in connection with FIG. 2 are overlaid on those portions of the anatomic map 70 for which diagnostic data has been collected. For example, in this case, the surgeon has already explored two branches of the left coronary artery and one branch of the right coronary artery. These diagnostic maps 56 appear on the anatomic map 70 in real time as the surgeon scans the lumen.

A surgeon can select a particular diagnostic map 56 on the anatomic map 70 by, for example, clicking on it. The diagnostic map 56 then appears in a detail window 72. Information descriptive of the selected diagnostic map 56 also appears in a map-information window 74 near the detail window 72.

Before beginning a scanning procedure, the surgeon clicks on a portion of the anatomic map 70 that corresponds to the artery to be scanned. If that portion has been previously scanned, the diagnostic map 56 of that previous scan appears on the detail window 72. If that portion has not been previously scanned, the detail window 72 is empty.

As the surgeon scans that portion of the artery, diagnostic data appears both in the detail window 72 and in that portion of the anatomic map 70 that corresponds to the artery being scanned. A cursor 76 within the detail window 72 indicates the relative location of the portion of the arterial wall 18 being scanned.

The cursor 76 is a strip extending horizontally, across the detail window 72, in which case the cursor 76 moves vertically up and down the detail window 72. This vertical motion of the cursor 76 reflects translation of the catheter 12 along the artery. As the cursor 76 slides vertically, it leaves in its wake 78 recently acquired diagnostic data. On the other side 80 of the cursor 76, the detail window 72 is either blank, or as is shown in FIG. 6, it shows a portion of a diagnostic map 56 from an earlier scan of that arterial wall 18.

Figure 8:
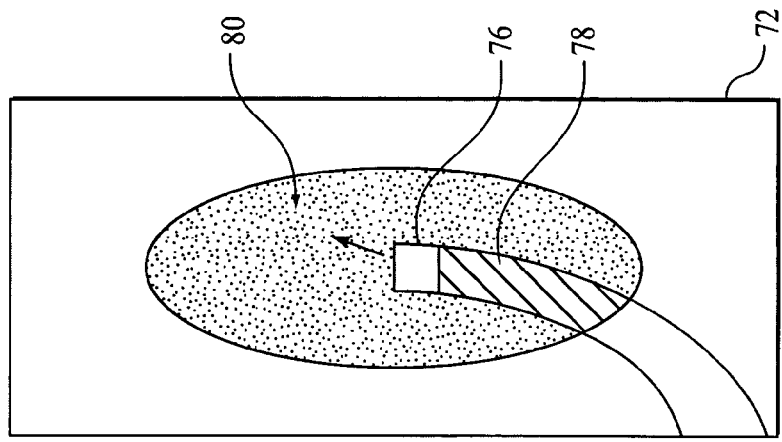
FIG. 8 shows a cursor having a shape corresponding to a field of view of the optical bench assembly.
Figure 7:
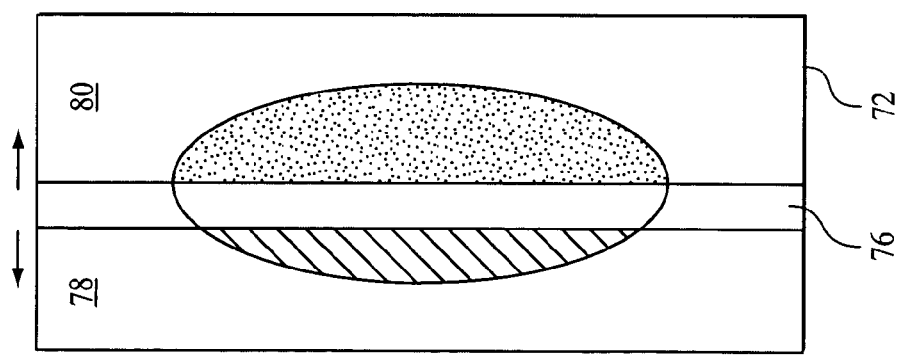
FIG. 7 shows a strip-shaped cursor.

Alternatively, the cursor 76 can appear as a strip extending vertically along the detail window 72, as shown in FIG. 7. In this case, the strip moves horizontally to form the diagnostic map 56. The horizontal motion of the cursor 76 in this case reflects rotation of the catheter 12. As the cursor 76 slides horizontally, it leaves in its wake 78 recently acquired diagnostic data. On the other side 80 of the cursor 76, the detail window 72 is either blank, or, as is shown in FIG. 7, it shows a portion of a diagnostic map 56 from an earlier scan of that artery In another embodiment, shown in FIG. 8, the cursor 76 is a region having a size and shape that corresponds to the field-of-view of the optical bench assembly 22. In this case, the cursor 76 moves horizontally, vertically, or both, in response to the surgeon's manipulation of the handle 42. As the cursor 76 moves, it leaves in its wake 78 recently acquired diagnostic data. In this embodiment, the diagnostic map 56 appears to be painted onto the detail window 72 by the movement of the cursor 76.

In either of the three embodiments described above, the surgeon retains the option of re-scanning a portion of the arterial wall 18 at any time. The surgeon does so by manipulating the handle 42 to move the cursor 76 over a portion of the detail window 72 that already shows diagnostic data from a previous scan of the arterial wall 18.

The structure and operation of the catheter 12 described herein are not affected by the type of diagnostic data collected by the catheter 12. The diagnostic data can be, for example, data that forms an image of the wall. Or, the diagnostic data can be spectroscopic data that represents the wall's response to illumination at one or more wavelengths. The diagnostic data can be acquired at optical, infrared, near-infrared, or any other wavelength. In particular, illumination of the arterial wall 18 at near IR wavelengths and collection of light scattered from the wall 18 is useful for identifying vulnerable plaque in the arterial wall 18.

In addition, the diagnostic data need not be electromagnetic in nature. The methods and devices disclosed herein are equally applicable to acquisition of, for example, ultrasonic data.

As described herein, the diagnostic map 56 is a two-dimensional map. The map is a two-dimensional map in part because the actuator provides movement with two degrees of freedom. However, the diagnostic map can also be a one-dimensional map. For example, an effectively one-dimensional map can be created by fixing the axial location and rotating the catheter. Conversely, the diagnostic map can be made a three-dimensional map by providing the actuator with a third degree of freedom of movement and by coupling the actuator to a position encoder for encoding movement associated with that third degree of freedom.

The diagnostic map 56 discussed herein shows spatial variation of a single quantity. However, the diagnostic map 56 can be used to show spatial variations of two or more quantities. For example, the two quantities may appear as different colors with intensities corresponding to the values of those quantities. Or one quantity may be represented as color while the other is represented by contours of constant value. Or alphanumerical characters representing values of one or more quantities can be superimposed on a diagnostic map 56 in which values of the other quantity are represented graphically. Or, alphanumeric characters representing values of one or more quantities can be made to appear in a window as a mouse or other selection device moves over the diagnostic map 56.

A catheter incorporating the position encoding structures and methods described herein is not restricted to one that scans the arterial wall with infrared light to identify vulnerable plaque. It will be apparent that such catheters can be used for a variety of applications. For example, a catheter may have an active portion that, instead of delivering or sensing infrared radiation, delivers or senses radiation at another range of frequencies. Or, the catheter may have an active portion that mechanically ablates structures on the wall, or that delivers drugs to a selected site.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A system for displaying diagnostic data, the system having a display on which is displayed an image comprising:
   an anatomic map; and
   a diagnostic map showing a spatial distribution of the diagnostic data, the diagnostic map being disposed on the anatomic map at a location indicative of the spatial distribution of the diagnostic data.

2. The system of claim 1, wherein the image further comprises a detail portion spatially removed from the anatomic map, the detail portion showing a detailed view of a diagnostic map disposed on a portion of the anatomic map.

3. The system of claim 2, further comprising selection means for selecting the portion of the anatomic map on which is disposed the diagnostic map to be displayed in the detail portion.

4. The system of claim 1, wherein the system is configured to display the diagnostic map concurrently with acquisition of the diagnostic data.

5. The system of claim 4, wherein the image further comprises a cursor configured to move relative to the diagnostic map, the position of the cursor relative the diagnostic map being indicative of a spatial location at which diagnostic data is currently being acquired.

6. The system of claim 1, wherein the diagnostic map changes in real-time as diagnostic data is acquired.

7. A computer-readable medium having encoded thereon software for causing a computer to display a spatial distribution of diagnostic data, the software comprising instructions for causing a computer to:
   display an anatomic map; and to
   overlay, at a location indicative of a spatial distribution of the diagnostic data on the anatomic map, a diagnostic map.

8. The computer-readable medium of claim 7, wherein the software further comprises instructions for causing the computer to display a detail portion spatially removed from the anatomic map, the detail portion showing a detailed view of a diagnostic map disposed on a portion of the anatomic map.

9. The computer-readable medium of claim 8, wherein the software further comprises instructions for causing the computer to select the portion of the anatomic map on which is disposed the diagnostic map to be displayed in the detail portion.

10. The computer-readable medium of claim 7, wherein the software further comprises instructions for causing the computer to display the diagnostic map concurrently with acquisition of the diagnostic data.

11. The computer-readable medium of claim 10, wherein the software further comprises instructions for causing a cursor to move relative to the diagnostic map, the position of the cursor relative the diagnostic map being indicative of a spatial location at which diagnostic data is currently being acquired.

12. The computer-readable medium of claim 7, wherein the instructions for causing a computer to overlay a diagnostic map comprise instructions to change the diagnostic map in real-time in response to acquisition of diagnostic data.

* * * * *